United States Patent [19]
Shah et al.

[11] Patent Number: 6,025,492
[45] Date of Patent: Feb. 15, 2000

[54] SYNTHESIS OF A HYDRAZONE β-KETO ESTER BY THE REACTION WITH A DIAZO ESTER

[75] Inventors: Ajit S. Shah, St. Louis, Mo.; Jerry D. Clark, Alton, Ill.; Yinong Ma, Westfield, Mass.; James C. Peterson, Manchester; Lefteris Patelis, Creve Coeur, both of Mo.

[73] Assignee: Monsanto Company, St. Louis, Mo.

[21] Appl. No.: 09/254,016

[22] PCT Filed: Aug. 29, 1997

[86] PCT No.: PCT/US97/15345

§ 371 Date: May 24, 1999

§ 102(e) Date: May 24, 1999

[87] PCT Pub. No.: WO98/08807

PCT Pub. Date: Mar. 5, 1998

Related U.S. Application Data

[60] Provisional application No. 60/024,963, Aug. 30, 1996, and provisional application No. 60/043,455, Apr. 10, 1997.

[51] Int. Cl.$^7$ ............ C07D 237/24; C07D 409/04; C07D 405/04; C07D 401/04; C07C 229/22
[52] U.S. Cl. ............ 544/239; 544/238; 560/34; 560/145; 560/169
[58] Field of Search ............ 560/34, 145, 169; 544/239

[56] References Cited

U.S. PATENT DOCUMENTS

| | | | |
|---|---|---|---|
| 4,707,181 | 11/1987 | Patterson | 71/92 |
| 4,962,199 | 10/1990 | Yalamanchili | 544/239 |
| 5,189,163 | 2/1993 | Cox et al. | 544/239 |

OTHER PUBLICATIONS

Abbass, Ikhlass M. et al. (1992) "Synthesis of Pyrazolo [4,5}pyridazine and Isoxazolo [3,4d]pyridazine Derivatives," *Arch. Pharm. Res.* 15(3):224–228.

Holmquist, Christopher R. et al. (1989) "A Selective Method for the Direct Conversion of Aldehydes into β–Keto Esters with Ethyl Diazoacetate Catalyzed by Tin(II) Chloride," *J. Org. Chem.* 54(14):3258–3260.

*Primary Examiner*—Michael G. Ambrose
*Attorney, Agent, or Firm*—Arnold White & Durkee

[57] ABSTRACT

The present invention relates to the synthesis of a hydrazone β-keto ester by the reaction of an alkyl diazoester with a hydrazone aldehyde in the presence of a Lewis acid In a preferred embodiment, the hydrazone β-keto ester is then converted into a pyridazinone compound by the reaction with an alkyl acid chloride in the presence of a base, followed by acidification. A process for the production of a hydrazone aldehyde, which comprises contacting a hydrazine and glyoxal, is also described.

23 Claims, No Drawings

SYNTHESIS OF A HYDRAZONE β-KETO ESTER BY THE REACTION WITH A DIAZO ESTER

The present application claims the benefit of U.S. Provisional Application Ser. Nos. 60/024,963, filed Aug. 30, 1996 and 60/043,455, filed Apr. 10, 1997.

BACKGROUND OF THE INVENTION

1. Field of the Invention

The present invention relates generally to a process for making pyridazinone derivatives and a hydrazone aldehyde precursor.

2. Description of Related Art

Certain carboxy substituted 4-oxo-1,4-dihydropyridazines and carboalkoxy substituted 4-oxo-1,4-dihydropyridazines are known in the art to have plant gametocidal activity and plant growth regulatory activity. Current methods for producing the above compounds typically use expensive raw materials and/or result in low yields of product. For example, U.S. Pat. Nos. 4,707,181; 5,026,880; and 4,732,603 disclose preparing the above compounds by reacting a 2-phenylhydrazono-3-oxoglutarate with an organic acid chloride in the presence of a Grignard reagent (isopropyl magnesium chloride). The Grignard reagents are expensive and low yields are obtained. U.S. Pat. Nos. 5,189,163 and 5,010,192 also disclose using expensive raw materials, such as methyl-3-oxopentanoate, and result in low yields.

The present invention provides a more efficient process for making pyridazinone derivatives which results in higher yields of product and uses lower cost raw materials, hydrazone aldehyde and diazo acetate.

Hydrazone aldehydes are useful as precursors in the production of the carboxy substituted 4-oxo-1,4-dihydropyridazines and carboalkoxy substituted 4-oxo-1,4-dihydropyridazines mentioned above. Such hydrazone aldehydes, such as 4-chlorophenylhydrazone aldehyde (ethanedial, mono[(4-chlorophenyl)hydrazone]), have typically been made by batch processes, wherein one reactant is added to a reactor containing the other reactant. However, such batch processes lead to a lower payload (2–5%). An increase in the payload above 5% made the reaction slurry difficult to mix and thus resulted in by-product formation. In addition, the water content of the resulting solution is about 80% in a batch process, making the solution difficult to wash and handle, and causing filtration of the product to be very slow. The high water content also leads to very long drying times of the product.

An improved process to produce hydrazone aldehydes having a decreased water content would lead to a solution which is easier to handle, and decreased filtration and drying times of the product.

SUMMARY OF THE INVENTION

The present invention relates to the synthesis of a hydrazone β-keto ester by the reaction of a diazo ester with a hydrazone aldehyde in the presence of a Lewis acid. In a preferred embodiment, the hydrazone β-keto ester is then converted into a pyridazinone compound by the reaction with an alkyl acid chloride in the presence of a base, followed by acidification.

More particularly, the present invention relates to the synthesis of a hydrazone β-keto ester having the general Formula III:

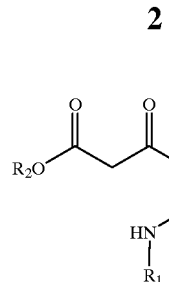

Formula III by reacting a diazo ester with a hydrazone aldehyde in the presence of a Lewis acid.

The hydrazone β-keto ester can then be reacted with an alkyl acid chloride in the presence of a base, followed by acidification to produce pyridazinone compounds having the general Formula I:

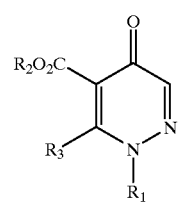

Formula I or the general Formula II:

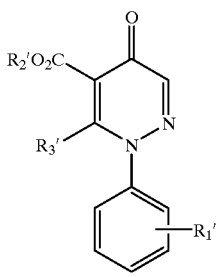

Formula II

The present invention also relates to a continuous process for the production of a hydrazone aldehyde comprising contacting a hydrazine and glyoxal, wherein the hydrazine and the glyoxal are added simultaneously to a reactor at a controlled rate, preferably between about 10 mL/min and about 100 mL/min.

DESCRIPTION OF ILLUSTRATIVE EMBODIMENTS

The present invention relates generally to a process for making pyridazinone derivatives and preferably to a process for making a compound of Formula I:

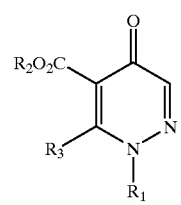

Formula I wherein $R_1$ is an alkyl, cycloalkyl, aryl or heteroaromatic group; $R_2$ is an alkyl group; and $R_3$ is an alkyl or phenyl group. Alkyl groups useful in the processes of the present invention include straight-chain, branched-chain or cyclic alkyl groups having between about 1 and 12 carbon atoms. Preferably the alkyl groups have from 1 to about 5 carbon atoms. Aryl in a given case can be phenyl and can be substituted with one or more lower alkyl groups and/or one or more halogen atoms such as Cl, Br or F and/or lower alkoxy group. Heteroaromatic groups include: furanyl, thienyl, pyridyl, etc., and can be optionally substituted as described in the case of phenyl groups.

In a preferred embodiment, the present invention relates to the production of pyridazinone compounds of Formula II:

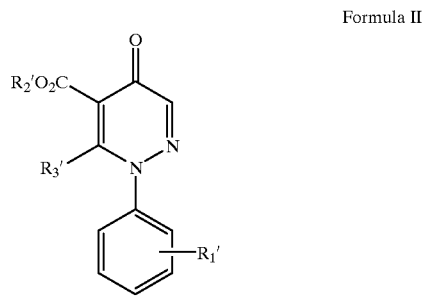

Formula II wherein $R_1'$ is an alkyl and/or halo group, $R_2'$ is an alkyl group and $R_3'$ is an alkyl or phenyl group.

The pyridazinone compounds of Formula I and II have plant gametocidal activity and plant growth regulatory activity. In the process of producing the pyridazinone compounds of Formula I and II, a β-keto ester is produced by reacting a hydrazone aldehyde with a diazo ester in the presence of a Lewis acid. The β-keto ester has the general Formula III:

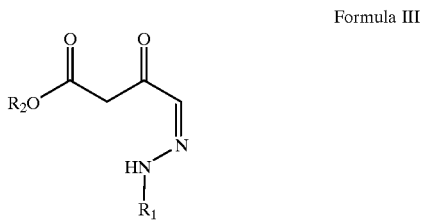

Formula III wherein $R_1$ and $R_2$ are as previously described. β-Keto esters can also be used in the synthesis of pyrazoles, which are used to prepare drugs, dyes and crop protection agents. The reaction can be generally described as follows:

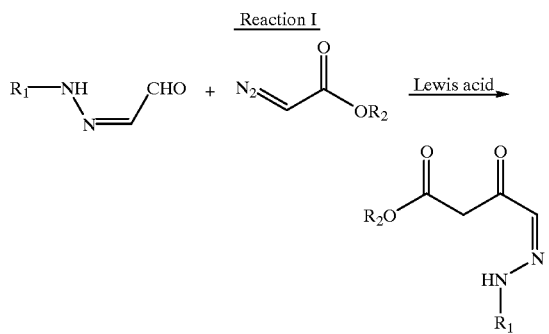

Reaction I wherein $R_1$ and $R_2$ are as previously described.

The reaction of the hydrazone aldehyde and alkyl diazoester to produce a β-keto ester can be conducted in the presence of a solvent. Solvents useful in the reaction of hydrazone aldehyde with diazo ester include organic solvents such as toluene, cumene, benzene, ethylbenzene, diethyl ether, dibutyl ether, butyl ethyl ether, chlorobenzene, nitrobenzene, ortho-dichlorobenzene, and chlorinated hydrocarbons such as methylene chloride and dichloroethane.

Alkyl diazoesters used in Reaction I to produce the β-keto ester are commercially available, such as from Aldrich Chemical Co., or can be produced as disclosed in U.S. Pat. Nos. 2,490,714; 2,691,649; and 2,691,650.

The hydrazone aldehyde can be added as a solid or in a slurry. Lewis acids suitable for use in this reaction have been previously described. For example, see Holmquist, C. R.; Roskamp, E. J. J. Org. Chem. 1989, 54, 3258. Lewis acids which are suitable in this reaction include $SnCl_2$, $ZnCl_2$, $ZrCl_4$, $AlCl_3$, $TiCl_4$, $SnCl_4$, $ZrCl_4$ $(THF)_2$, zeolites, $SnCl_2+$ triphenylmethyl chloride (TMSCl), and $SnCl_2+TMSCl$. Mixtures of Lewis acids can also be used. Preferred Lewis acids are $SnCl_2$ and $SnCl_4$, and the Lewis acid should be present in a catalytic amount, typically between about 5 mol % and 25 mol %. The reaction is generally started at a temperature below room temperature, typically between about 0° C. and about 25° C., and gradually allowed to warm to room temperature during the course of the reaction. The hydrazone aldehyde and diazo ester are typically added in approximately stoichiometric proportions, although ratios of hydrazone aldehyde to diazo ester of about 2:1 to about 1:2 can also be used.

The β-keto ester is then treated with a base and an alkyl acid halide, followed by acidification, to produce a compound of Formula I as shown below:

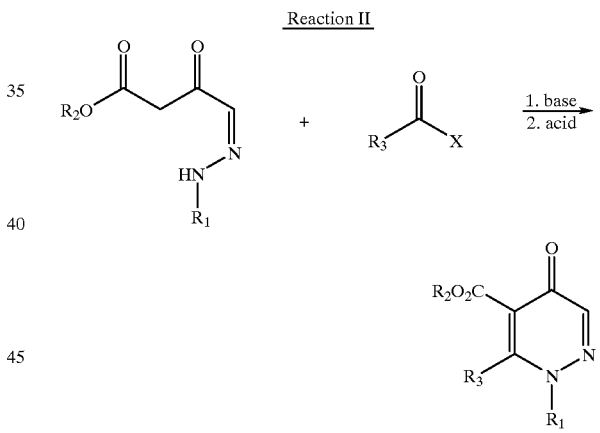

Reaction II wherein $R_1$, $R_2$ and $R_3$ are as described previously, and X is a halide, preferably chloro or bromo.

Reaction II of the β-keto ester with an alkyl acid halide and base can also be conducted in the presence of a solvent as described above. The β-keto ester can be purified prior to use in this reaction or can be used directly from Reaction I without purification. Bases useful in this reaction are generally described below, and a preferred base is $Ca(OH)_2$. A preferred alkyl acid halide suitable in this reaction is propionyl chloride. Reaction II can also be conducted in the presence of an acylation catalyst, such as pyridine or a substituted pyridine, preferably 4-dimethylaminopyridine (DMAP), polymer-supported DMAP, or 4-(4-methyl-1,1-piperidinyl)pyridine. Acids useful in the acidification that follows are generally any acid known for such acidification, and the acid is preferably HCl, $H_2SO_4$ or $H_3PO_4$.

Reaction II is preferably conducted at a temperature between about 0° C. and about 40° C. The acid halide and base are generally added in slight excess, such that the ratio of acid halide to b-keto ester or the ratio of base to b-keto ester is between about 1:1 to about 3:1. The acylation catalyst can be used in an amount between about 0 and 15 mol %, preferably between about 8 and 10 mol %.

Bases which can be used in the processes of the present invention include both organic and inorganic bases. Suitable inorganic bases include Group I and II metal hydrides, hydroxides and oxides, such as sodium hydride, calcium hydroxide, calcium oxide, barium hydroxide, barium oxide, magnesium hydroxide, magnesium oxide and the like. Suitable organic bases include both alkyl and aromatic bases such as alkyl, cycloalkyl and aryl amines, metallic amides and aromatic amines. Suitable alkyl and aryl amines include diethylamine, triethylamine, benzylamine, piperidine, piperazine, pyrrolidine and the like. Alkylamines, such as triethylamines, are preferred. Suitable metallic amides include sodium amide and lithium diisopropyl amide. Suitable aromatic amines (aromatic, nitrogen heterocylic compounds) include imidazole, methylimidazole, pyrazole, pyridine, pyrimidine, pyridazine and the like, preferably pyridines. Those skilled in the art will appreciate that other bases can be utilized in the process of the present invention.

As an initial matter, the hydrazone aldehyde used in Reaction I to produce the β-keto ester can be made from a hydrazine. For instance, a substituted hydrazine can be reacted in the presence of a glyoxal solution to form a hydrazone aldehyde:

Reaction III

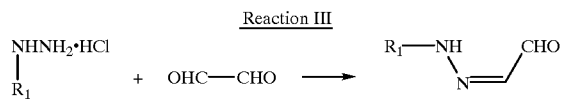

wherein $R_1$ is as previously described. The hydrazone aldehyde can be made by either a batch or continuous process, preferably by a continuous process. It has been found that when a hydrazine and glyoxal are contacted in a continuous process, such that the reactants are added simultaneously at a controlled rate near one another in physical proximity, the resulting hydrazone aldehyde composition comprises less than about 50% by weight water, compared to about 80% by water occasioned in a batch process. Such reduction in water content leads to easier handling of the product and decreased filtration and drying times. Typical flowrates for the addition of the hydrazine and glyoxal are between about 10 and 100 mL/min, preferably between about 10 and 50 mL/min. The ratio of the hydrazine to glyoxal is generally between about 1:1 to 1:1.5, preferably between about 1:1 and 1:1.25

The continuous process of Reaction III can be conducted in any type of continuous reactor, preferably a continuous stirred tank reactor (CSTR). The temperature of the hydrazone aldehyde synthesis in the continuous process is generally between about 40° C. and 70° C., preferably between about 50° C. and 70° C. When a batch process is used for Reaction III, the temperature is generally at or below room temperature, and one reactant is added to a batch reactor containing the other reactant. Hydrazone aldehydes are also useful as precursors in the production of certain carboxy substituted 4-oxo-1,4-dihydropyridazines and carboalkoxy substituted 4-oxo-1,4-dihydropyridazines, which are known to have gametocidal activity.

A compound of the general Formula I can be converted to the acid and then the salt form using standard procedures, such as those disclosed in U.S. Pat. No. 5,026,880. For example, the solid free acid can be made by treatment of the compound of Formula I with NaOH, followed by acidification with HCl:

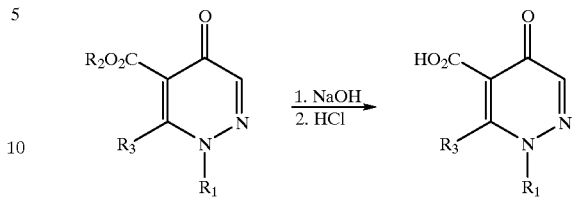

The potassium salt can subsequently be made by treatment of the free acid with KOH.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

This example illustrates Reaction III, the production of a hydrazone aldehyde from a hydrazine, in a batch process.

To a mixture of 100.0 g (0.56 mol) of 4-chlorophenylhydrazine hydrochloride in 2000 mL of water was added 167.7 g (1.15 mol) of a 40% glyoxal solution in water along with 500 mL of water. The stirred slurry was maintained at 15–20° C. for 4 h. The hydrazone was then filtered and dried to yield 94 g (92.5% yield) of yellow solid, m.p. 150–15° C. The product was ethanedial, mono[(4-chlorophenyl)hydrazone], as characterized by $^1$H NMR.

EXAMPLE 2

This example illustrates Reaction I, the production of a β-keto ester by reacting a hydrazone aldehyde and diazo ester in the presence of a Lewis acid.

To a slurry of 10.3 g (0.06 mol) of hydrazone aldehyde (ethanedial, mono[(4-chlorophenyl)hydrazone]) in 600 mL of methylene chloride at 25° C., 2.55 g (0.014 mol) of tin(II) chloride was added. Then, 6.78 g (0.06 mol) of ethyldiazo acetate was added. The reaction was stirred for 18 h at 25° C. The reaction mixture was diluted with 100 mL of methylene chloride and to the resulting mixture was added 100 mL of water. After stirring for 5 minutes, the mixture was filtered through celite and the methylene chloride layer was separated and concentrated under reduced pressure to obtain a dark brown residue. The product, butanoic acid (4-[(4-chlorophenyl)-(1-hydrazinyl-2-ylidene)]-3-oxo-) ethyl ester, was purified by crystallization from ether and hexane as a yellow solid (8.20 g, 54.2% yield), m.p. 100–100.5° C.

EXAMPLE 3

This example illustrates Reaction II, wherein a β-keto ester is reacted with an alkyl acid halide to produce a pyridazinone compound having the general Formula I.

A solution of 0.5 g (1.87 mmol) of the β-keto ester produced in Example 8 in 10 mL of toluene was treated with 0.21 g (2.79 mmol) of Ca(OH)$_2$. The slurry was stirred for 2 h at 25° C. Propionyl chloride (0.25 g, 2.79 mmol) was then added slowly, and the reaction was stirred for 5h at 25° C.

At this time 10 mL of water and 20 mL of 5N HCl was added, and the reaction was stirred for 30 minutes to solubilize the calcium salts.

The top toluene layer was separated (the bottom aqueous layer was discarded) and heated to 80° C. for 2 h. After cooling excess solvent was removed under reduced pressure to yield 0.57 g of an amber solid. This product was 95% pure by $^1$H NMR (99.8% yield). 180 mg of the crude product was purified by chromatography (silica gel, 50% ethyl acetate in hexane) to yield 160 mg of pure product, 4-pyridazinecarboxylic acid (2-(4-chlorophenyl)-3-ethyl-2, 5-dihydro-5-oxo-) ethyl ester, as a yellow solid, m.p. 130–131° C.

EXAMPLE 4

This example illustrates the synthesis of a β-keto ester from hydrazone aldehyde and ethyl diazoacetate, shown in the reaction below:

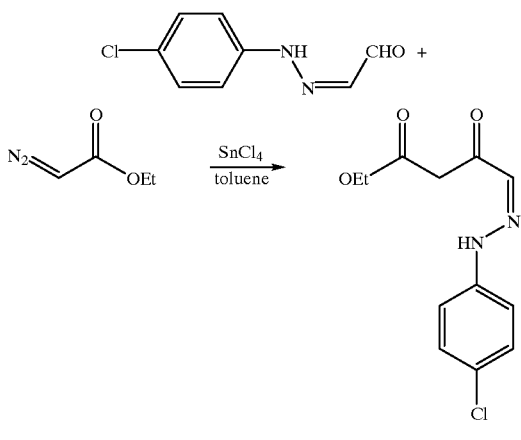

A dry reactor is charged with 162.2 g of a solution of 10.0 wt-% ethyl diazoacetate in toluene, and 20.0 g of [(4-chlorophenyl)hydrazono] acetaldehyde. The slurry is then cooled to 0° C.

To the cooled slurry is added 8.09 mL of 1.00 M tin (IV) chloride solution in toluene over a period of 80 min. The temperature of the slurry is maintained below 5° C. during the addition.

The mixture is then allowed to warm to room temperature and is stirred for an additional 2 hours. The reaction is monitored by HPLC analysis. Chemical yield is about 67.5%. All of the hydrazone aldehyde is consumed.

EXAMPLE 5

This example illustrates the synthesis of a diketo ester from a β-keto ester, shown in the reaction below:

To the agitated crude reaction mixture at 22° C. from Example 4, is added 8.45 g of calcium hydroxide. The reactor is then charged with 1.34 g of 4-dimethylaminopyridine (DMAP).

Propionyl chloride (9.81 g ) is then added over a period of 10 min. The temperature of the mixture increases from 28to 32° C. The reaction is complete after the propionyl chloride is added based on HPLC analysis. The chemical yield is about 90%.

EXAMPLE 6

This example illustrates the synthesis of the ethyl ester from the diketo ester of Example 6, shown in the reaction below:

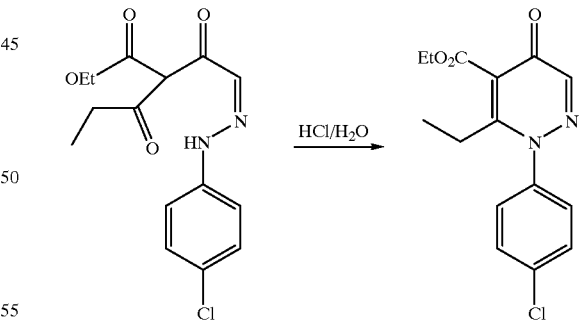

To the vigorously agitated crude reaction mixture from Example 5 is added 68 mL of 1.2 N HCl (aq.). The biphasic system is heated to 80° C. and this temperature is maintained for 1 hour. The reaction is complete based on HPLC analysis.

The contents are filtered at 80° C. to remove insoluble materials that are suspended in the aqueous layer. The filtration is complete within 1 h. The aqueous layer is separated from the organic layer, and the organic layer (top) (191 g) contains the ethyl ester, and can then be used to produce the free acid. The aqueous layer (bottom) is discarded. The chemical yield is about 90%.

EXAMPLE 7

This example illustrates the synthesis of the free acid of the ethyl ester of Example 6 via saponification and acidification, shown in the reaction below:

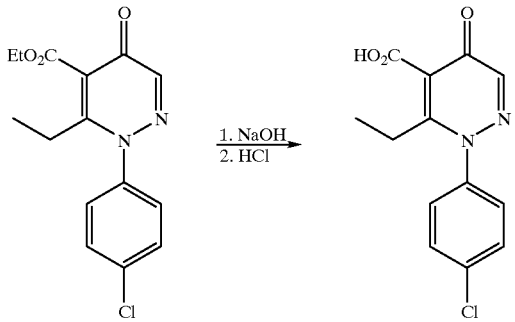

To the vigorously agitated reaction mixture from Example 7, is added 137 g of 15% w/w aqueous sodium hydroxide solution. The biphasic system is heated to 60° C. and is stirred for 2 h. The layers are separated. The top organic phase is discarded. The bottom aqueous layer (165 g) is treated with 100 mL isopropanol.

To this mixture is added 50 mL of concentrated hydrochloric acid (37% wt) over 10 min. The resulting mixture is cooled to room temperature while stirring (30 min). The contents are filtered, and the filtered cake is washed with 50 mL of isopropanol. The chemical yield is about 95%. After air drying, 13 g of solid with greater than 95% purity of the free acid was isolated, as characterized by $^1$H and $^{13}$C NMR.

EXAMPLE 8

This example illustrates the synthesis of hydrazone aldehyde in a continuous process, shown in the reaction below:

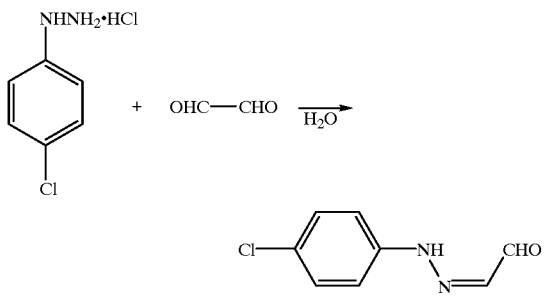

4-Chlorophenylhydrazine hydrochloride (21.77 g, 0.12 mole) is dissolved in 600 mL of hot DI water (60° C.). The solution is then filtered to remove the insoluble materials and the solution volume is adjusted to 600 mL and maintained at 60° C. Glyoxal (40% by wt., 21.75 g, 0.15 moles) is diluted in 600 mL of water and is preheated to 60° C. In the CSTR (Continuous Stirred Tank Reactor) 300 mL of DI water is charged and preheated to 60° C. The solutions of hydrazine as well as glyoxal are continuously added to the stirred reactor (agitation speed, 300 rpm) at the rate of 24 mL/minute. The reaction temperature (60° C.) in the reactor was maintained by external heating. The overflow was continuously filtered using a Buchner funnel. After the complete addition of glyoxal and hydrazine solution, the reaction mixture was allowed to stir at 60° C. for another 25 minutes and then filtered. The wet cake was light yellow in color and filtration was very fast. The cake was washed twice with DI water (50 mL each) and sucked dry under vacuum. After about 18 h, the moisture content of the wet cake was 0.15%. Total mass of the product was 20.0 g (92% yield, assay 99.5%).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A process for the production of a hydrazone β-keto ester of Formula III:

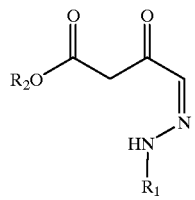

Formula III wherein $R_1$ is an alkyl, cycloalkyl, aryl or heteroaromatic group; and $R_2$ is an alkyl group; comprising contacting a diazo ester of the formula

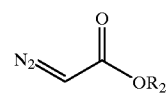

with a hydrazone aldehyde of the formula

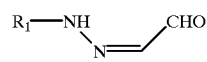

in the presence of a Lewis acid.

2. The process of claim 1 wherein the diazo ester is an alkyl or benzyl diazo acetate.

3. The process of claim 2 wherein the diazo ester is ethyl diazo acetate.

4. The process of claim 2 wherein the diazo ester is isopropyl diazo acetate.

5. The process of claim 1 wherein the Lewis acid is a tin(II) or tin(IV) compound.

6. The process of claim 5 wherein the Lewis acid is $SnCl_2$ or $SnCl_4$.

7. The process of claim 1 wherein the contacting is conducted in the presence of an organic solvent.

8. The process of claim 7 wherein the solvent is toluene, cumene, benzene, ethylbenzene, diethyl ether, dibutyl ether, butyl ethyl ether, chlorobenzene, nitrobenzene, ortho-dichlorobenzene, methylene chloride or dichloroethane.

9. The process of claim 1 wherein the contacting is conducted at a temperature between about 0° C. and 25° C.

10. The process of claim 1 wherein the hydrazone aldehyde and diazo ester are added in a ratio of between about 1:2 and about 2:1.

11. The process of claim 1 wherein the hydrazone aldehyde is ethanedial, mono[(4-chlorophenyl)hydrazone].

12. A process for the production of a pyridazinone compound of formula I:

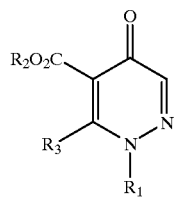

Formula I wherein $R_1$ is an alkyl, cycloalkyl, aryl or heteroaromatic group; $R_2$ is an alkyl group; and $R_3$ is an alkyl or phenyl group; comprising:

contacting a diazo ester of the formula

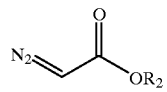

with a hydrazone aldehyde of the formula

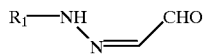

in the presence of a Lewis acid to produce a hydrazone β-keto ester of Formula III,

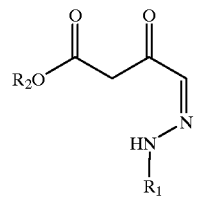

Formula III contacting the hydrazone β-keto ester with an alkyl acid halide in the presence of a base to form a diketo ester, and contacting the diketo ester with an acid.

13. The process of claim 12 wherein the hydrazone aldehyde is ethanedial, mono[(4-chlorophenyl)hydrazone].

14. The process of claim 12 wherein the Lewis acid is a tin(II) or tin(IV) compound.

15. The process of claim 14 wherein the Lewis acid is $SnCl_2$ or $SnCl_4$.

16. The process of claim 12 wherein the diazo ester is an alkyl or benzyl diazo acetate.

17. The process of claim 16 wherein the diazo ester is ethyl diazo acetate.

18. The process of claim 16 wherein the diazo ester is isopropyl diazo acetate.

19. The process of claim 12 wherein $R_1$ is an aryl group.

20. The process of claim 19 wherein the aryl group is a phenyl substituted with one or more lower alkyl groups and/or halogen atoms and/or lower alkoxy group.

21. The process of claim 12 wherein $R_1$ is a heteroaromatic group.

22. The process of claim 21 wherein the heteroaromatic group is selected from the group consisting of furanyl, thienyl and pyridyl.

23. The process of claim 21 wherein the heteroaromatic group is substituted with one or more lower alkyl groups and/or halogen atoms and/or lower alkoxy group.

* * * * *

UNITED STATES PATENT AND TRADEMARK OFFICE
CERTIFICATE OF CORRECTION

PATENT NO. : 6,025,492
DATED : February 15, 2000
INVENTOR(S) : Ajit S. Shah, Jerry D. Clark, Yinong Ma, James C. Patterson, Lefteris Patelis It is certified that error appears in the above-identified patent and that said Letters Patent is hereby corrected as shown below:

Claims,
Please add the following claims:
-- 24. The process of claim 12 where said pyridazinone compound is of Formula II:

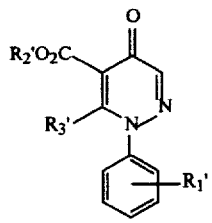

Formula II wherein $R_1'$ is an alkyl and/or halo group, $R_2'$ is an alkyl group and $R_3'$ is an alkyl or phenyl group.

25. The process of claim 24 wherein $R_1'$ is a chloride, $R_2'$ is ethyl, and $R_3'$ is ethyl.
26. The process of claim 24 wherein the diazo ester is an alkyl or benzyl diazo acetate.
27. The process of claim 26 wherein the diazo ester is ethyl diazo acetate.
28. The process of claim 27 wherein the diazo ester is isopropyl diazo acetate. --

Signed and Sealed this

Nineteenth Day of February, 2002

Attest:

Attesting Officer

JAMES E. ROGAN
Director of the United States Patent and Trademark Office